US010959926B2

(12) United States Patent
Krohn et al.

(10) Patent No.: US 10,959,926 B2
(45) Date of Patent: Mar. 30, 2021

(54) HAIR TREATMENT AGENT WITH A POLYVALENT METAL CATION I

(71) Applicant: Henkel AG & Co. KGaA, Duesseldorf (DE)

(72) Inventors: René Krohn, Norderstedt (DE); Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/118,165

(22) Filed: Aug. 30, 2018

(65) Prior Publication Data

US 2019/0070083 A1   Mar. 7, 2019

(30) Foreign Application Priority Data

Sep. 5, 2017   (DE) ..................... 10 2017 215 579.5

(51) Int. Cl.
*A61Q 5/00* (2006.01)
*A61K 8/36* (2006.01)
*A61K 8/28* (2006.01)
*A61K 8/19* (2006.01)
*A61K 8/362* (2006.01)
*A61K 8/41* (2006.01)
*A61K 8/60* (2006.01)
*A61Q 5/02* (2006.01)
*A61Q 5/12* (2006.01)

(52) U.S. Cl.
CPC ............... *A61K 8/361* (2013.01); *A61K 8/19* (2013.01); *A61K 8/28* (2013.01); *A61K 8/362* (2013.01); *A61K 8/416* (2013.01); *A61K 8/604* (2013.01); *A61Q 5/004* (2013.01); *A61K 2800/5426* (2013.01); *A61Q 5/02* (2013.01); *A61Q 5/12* (2013.01)

(58) Field of Classification Search
None
See application file for complete search history.

(56) References Cited

U.S. PATENT DOCUMENTS 3,958,581 A * 5/1976 Abegg ..................... A61K 8/19
132/203
2014/0248229 A1 * 9/2014 Krueger .................. A61Q 5/12
424/70.17

FOREIGN PATENT DOCUMENTS

| EP | 1676604 A1 | 7/2006 | |
| FR | 2937539 A1 * | 4/2010 | ............ A61Q 5/004 |
| JP | 2000053541 A | 2/2000 | |
| JP | 2004107312 A | 4/2004 | |
| JP | 2016079165 A | 5/2016 | |
| WO | 9417777 A1 | 8/1994 | |
| WO | WO-9417777 A1 * | 8/1994 | ............ A61K 8/361 |
| WO | 9621425 A1 | 7/1996 | |

OTHER PUBLICATIONS

Intellectual Property Office, Search Report under Section 17(5) for United Kingdom Patent Application No. GB1814343.8 dated Mar. 11, 2019.

* cited by examiner

*Primary Examiner* — Brian Gulledge
(74) *Attorney, Agent, or Firm* — Lorenz & Kopf, LLP

(57) ABSTRACT

The subject matter of the present disclosure is a hair treatment agent for reducing and/or avoiding bleeding out and/or fading of artificially produced hair colours and/or for strengthening the internal hair structure, containing—relative to the total quantity of hair treatment agent—
 a) from about 1 to about 15 wt. % of a salt-containing component. comprising
  (i) at least one polyvalent salt of a fatty acid and/or
  (ii) at least one fatty acid (A1) and at least one polyvalent salt (A2).
 b) at least one cationic compound selected from
cationic tensides of the group formed from quaternary ammonium compounds, esterquats and/or amidoamines and/or
cationic polymers.

17 Claims, No Drawings

HAIR TREATMENT AGENT WITH A POLYVALENT METAL CATION I

CROSS-REFERENCE TO RELATED APPLICATION

This application claims priority to German Patent Application No. 10 2017 215 579.5, filed Sep. 5, 2017, which is incorporated herein by reference in its entirety.

TECHNICAL FIELD

The application relates to a hair treatment agent for reducing and/or avoiding the bleeding out and/or fading of artificially produced hair colours and/or for strengthening the internal hair structure with a polyvalent cation.

BACKGROUND

Products for changing the natural hair colour play an outstanding role in hair cosmetics. A distinction is made between permanent, semi-permanent or temporary colour systems based on chemical and/or natural dyes. However, the hair colours produced artificially by permanent, semi-permanent or temporary colour systems have the disadvantage that they can change in an undesirable manner—for example during or after hair washing.

"Undesirable change" is understood as the fading or bleeding out and also the loss of colour brilliance of the shade of the hair produced by the respective colouring. Environmental influences and/or effects of the sun can further intensify these changes. There is accordingly the need for hair treatment agents that can better stabilize artificially produced hair colours.

Hair treatment agents for protecting artificially produced hair colours or methods for stabilizing artificially produced hair colours are known in principle. A method for enhancing the chroma of hair is described in EP 1676604 A1 in which the hair is initially washed with a shampoo which contains a water-soluble salt—preferably sodium sulphate—in addition to an anionic tenside and a special silicone. In a second step the hair is treated with a conditioning agent comprising a long-chain alcohol and a cationic tenside in a specific weight ratio and then rinsed.

However the consumer desires less time-intensive methods to protect hair colours from any change preferably in one treatment step.

BRIEF SUMMARY

Hair treatment agents and methods for reducing and/or avoiding bleeding out and/or fading of dyed-blond and/or artificially produced hair colours and/or for strengthening the internal hair structure are provided herein. In an embodiment, a hair treatment agent for reducing and/or avoiding bleeding out and/or fading of artificially produced hair colours and/or for strengthening the internal hair structure is provided. The hair treatment agent includes, relative to the total quantity of hair treatment agent, from about 1 to about 15 wt. % of a salt-containing component and at least one cationic compound. The salt-containing component includes at least one polyvalent salt of a fatty acid and/or at least one fatty acid and at least one polyvalent salt. The at least one cationic compound is selected from cationic tensides selected from the group of quaternary ammonium compounds, esterquats and/or amidoamines and/or cationic polymers.

In another embodiment, a method for reducing and/or avoiding bleeding out and/or fading of dyed-blond and/or artificially produced hair colours and/or for strengthening the internal hair structure is provided. The method includes applying a hair treatment agent to the dyed-blond and/or coloured hair. The hair treatment agent is allowed to act for a period of at least about 5 seconds. Optionally, the agent is rinsed out of the hair with water. The hair treatment agent includes, relative to its weight, from about 1 to about 15 wt. % of a salt-containing component and at least one cationic compound. The salt-containing component includes at least one polyvalent salt of a fatty acid and/or at least one fatty acid and at least one polyvalent salt. The at least one cationic compound is selected from cationic tensides selected from the group of quaternary ammonium compounds, esterquats and/or amidoamines and/or cationic polymers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was to provide a hair treatment agent which can be used simply and rapidly to intensify the adhesion of dyes to the hair fibres and thus the genuineness of the artificially produced hair colour can be maintained.

The chemical treatment of hair during lightening or colouring as well as heat treatments brings about a breaking of fine bonds in the hair fibres and damages their internal structure.

Last but not least, due to the severe stressing of the hair, for example due to the colouring or permanent waving and also due to the washing of the hair with shampoos and due to environmental influences, the importance of care products with the longest-lasting effect is increasing. Such care produces influence the natural structure and the properties of the hair. Thus, for example, the wet and dry combability of the hair, the hold and fullness of the hair can then be optimized to such treatments or the hair can be protected from an increased split rate.

Ideally mild hair treatment agents should be provided which impart colour protection to the treated hair and reconstruct the damaged bonds in the hair fibres and thus reinforce the inner hair structure.

It was found that a hair treatment agent which contains a selected metal fatty acid soap or a selected fatty acid salt mixture in addition to a cationic component is exceptionally suitable for this.

A first subject matter of the present disclosure is therefore a hair treatment agent for reducing and/or avoiding bleeding out and/or fading of artificially produced hair colours and/or for strengthening the internal hair structure, containing—relative to the total quantity of hair treatment agent—
  a) from about 1 to about 15 wt. % of a salt-containing component, comprising
    (i) at least one polyvalent salt of a fatty acid and/or
    (ii) at least one fatty acid (A1) and at least one polyvalent salt (A2),
  b) at least one cationic compound selected from cationic tensides of the group formed from quaternary ammonium compounds, esterquats and/or amidoamines and/or cationic polymers.

Suitable hair treatment agents are preferably hair washing agents such as shampoos, hair care agents such as hair conditioners, rinses or hair care sprays as well as hair styling agents such as hair gels, hair sprays or hair wax. Preferably the hair treatment agent comprises a hair care agent. It is particularly preferable that the hair care agent is used following a dyeing blond, colouring and/or permanent deformation (permanent wave or straightening) of the hair.

The hair treatment agents necessarily contain from about 1 to about 10 wt. % of a salt-containing component a). Suitable polyvalent salts of a fatty acid (component a) (i)) which can be used in the hair treatment agents are preferably selected from the polyvalent salts of a fatty acid from the group formed from dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, palmitoleic acid, petroselinic acid, elaidinic acid, oleic acid, erucic acid, linoleic acid, linolenic acid and mixtures thereof. Particularly preferred is octadecanoic acid (stearic acid).

In addition to the fatty acid anion, the polyvalent salts (component a)(i)) preferably comprise the cations of strontium, zirconium, hafnium, titanium, tin, aluminium, bismuth and lanthanum. Particularly preferred are the cations of strontium, aluminium, zirconium and/or lanthanum. Quite particularly preferably the polyvalent salts of a fatty acid comprise $Sr^{2+}$, $Al^{3+}$, $Zr^{4+}$ and/or $La^{3+}$ as cations. A particularly preferred polyvalent salt of a fatty acid (component a)(i)) is strontium stearate. The polyvalent salt (component a)(i)) preferably contains a polyvalent cation which is divalent, trivalent or tetravalent.

Suitable components a)(ii) which can be used in the hair treatment agents are preferably selected from fatty acids (A1) from the group formed from dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, palmitoleic acid, petroselinic acid, elaidinic acid, oleic acid, erucic acid, linoleic acid, linolenic acid and mixtures thereof as well as from polyvalent salts (A2) whose anions are selected from the group of halides, hydroxides, sulphates, nitrates, triflates, borates, citrates, tartrates, lactates, malates, salicylates, aspartates, arginates, fumarates, maleates and mixtures thereof.

A particularly suitable salt (A1) is octadecanoic acid (stearic acid).

Suitable polyvalent salts (A2) are strontium, zirconium, hafnium, titanium, tin, aluminium, bismuth and/or lanthanum salts. Particularly suitable polyvalent salts (A2) are strontium, aluminium, zirconium and/or lanthanum halide, in particular strontium, aluminium, zirconium and/or lanthanum chloride, and/or strontium, aluminium, zirconium and/or lanthanum lactate.

The polyvalent salt (A2) preferably contains a polyvalent cation which is divalent, trivalent or tetravalent, more preferably trivalent or tetravalent and particularly preferably tetravalent.

In a further preferred embodiment, the hair treatment agent therefore contains as component a) (i) the strontium, aluminium, zirconium and/or lanthanum salts of a fatty acid, in particular the strontium, aluminium, zirconium and/or lanthanum salts of stearic acid. In a likewise preferred embodiment the hair treatment agent contains as component a)(ii)(A1) preferably a fatty acid, preferably stearic acid, and as component a)(ii)(A2) preferably a strontium, aluminium, zirconium and/or lanthanum halide, preferably lanthanum chloride. In a further likewise preferred embodiment the hair treatment agent preferably contains as component a)(ii)(A1) a fatty acid, preferably stearic acid and as component a)(ii)(A2) preferably a strontium, aluminium, zirconium and/or lanthanum lactate, preferably strontium lactate or aluminium lactate.

The hair treatment agents contain—relative to their weight—preferably from about 1.5 to about 15 wt. %, more preferably from about 1.8 to about 10 wt. % and even more preferably from about 2 to about 8 wt. % of the salt-containing component a)(i).

The hair treatment agents contain—relative to their weight—preferably from about 1 to about 10 wt. %, more preferably from about 1.5 to about 6 wt. % and even more preferably from about 2 to about 4 wt. % of fatty acid (A1) as constituent of the salt-containing component a)(ii).

The hair treatment agents contain—relative to their weight—preferably from about 0.01 to about 5 wt. %, more preferably form about 0.2 to about 4 wt. % and even more preferably from about 0.5 to about 3 wt. % of polyvalent salt (A2) as constituent of the salt-containing component a)(ii).

The hair treatment agents contain as second essential ingredient a selected cationic tenside and/or a cationic polymer.

The selected cationic tensides comprise quaternary ammonium compounds, esterquats and/or amidoamines.

Preferred quaternary ammonium compounds are ammonium halides, in particular chlorides or bromides such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride, as well as the imidazolinium compounds known under the INCI designations Quaternium-27, Quaternium-83 and Quaternium-87. The alkyl chains of the aforesaid tensides preferably have from about 10 to about 18 carbon atoms.

Esterquats are substances which contain both at least one ester function and also at least one quaternary ammonium group as structural element. Preferred esterquats are quaternated ester salts of fatty acids with triethanol amine, quaternated ester salts of fatty acids with diethanol alkylamines and quaternated ester salts of fatty acids with 1,2-dihydroxypropyl dialkylamines. Specific examples are methyl-N-(2-hydroxyethyl)-N,N-di(talgacyloxyethyl)ammonium compounds, bis-(palmitoyloxyethyl)hydroxy ethyl-methyl-ammonium compounds, methyl-N,N-bis(stearoyloxyethyl)-N-(2-hydroxyethyl)ammonium compounds, methyl-N,N-bis(cocoyloxyethyl)-N-(2-hydroxyethyl)ammonium compounds or N,N-dimethyl-N,N-di(talgacyloxyethyl)ammonium compounds. Such products are marketed under the designations Stepantex®, Dehyquart®, Armocare® and Quartamin®.

Alkyl amidoamines are usually produced by amidization of natural or synthetic fatty acids and fatty acid sections with dialkyl aminoamines. A particularly suitable compound from this substance group is the stearamidopropyl dimethylamine available commercially under the designation Tegoamid® S 18.

The cationic polymers can be homo- or copolymers or polymers based on natural polymers, wherein the quaternary nitrogen groups are contained either in the polymer chain or preferably as a substituent at one or several of the monomers. Suitable cationic monomers are unsaturated, radically polymerizable compounds which carry at least one cationic group, in particular ammonium substituted vinyl monomer, s such as, for example, trialkylmethacryloxy-alkylammonium, trialkyl acryloxyalkyl ammonium, dialkyl diallyl ammonium and quaternary vinyl ammonium monomers with cyclic groups containing cationic nitrogens such as pyridinium, imidazolium or quaternary pyrrolidone, e.g. alkylvinyl imidazolium, alkylvinyl pyridinium, or alkylvinyl pyrrolidone salts. The alkyl groups of these monomers are preferably lower alkyl groups such as, for example C1 to C7 alkyl groups, particularly preferably C1 to C3-alkyl groups.

The monomers containing ammonium groups can be copolymerized with non-cationic monomers. Suitable comonomers are for example acrylamide, methacrylamide; alkyl- and dialkyl acrylamide, alkyl- and dialkyl methacrylamide, alkylacrylate, alkyl methacrylate, vinyl caprolactone, vinyl caprolactam, vinyl pyrrolidone, vinylester, e.g. vinyl acetate, vinyl alcohol, propylene glycol or ethylene glycol, wherein the alkyl groups of these monomers are preferably C1 to C7 alkyl groups, particularly preferably C1 to C3 alkyl groups.

From the plurality of these polymers, the following have proved particularly suitable:
homopolymers having the general formula

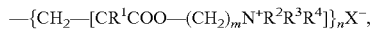

where $R^1$=—H or —$CH_3$, $R^2$, $R^3$ and $R^4$ are selected independently of one another from C1-4-alkyl, -alkenyl or hydroxyalkyl groups, m=1, 2, 3 or 4, n is a natural number and
$X^-$ is a physiologically compatible organic or inorganic anion. Within the framework of these polymers those for which one of the following conditions applies are preferred: $R^1$ stands for a methyl group, $R^2$, $R^3$ and $R^4$ stand for methyl groups, m has the value 2.

Halide ions, sulphate ions, phosphate ions, methosulphate ions as well as organic ions such as lactate, citrate, tartrate and acetate ions come into consideration as physiologically compatible counter-ions $X^-$. Preferred are methosulphates and halide ions, in particular chloride.

Suitable cationic polymers are for example copolymers according to the formula (Copo).

Formula (Copo)

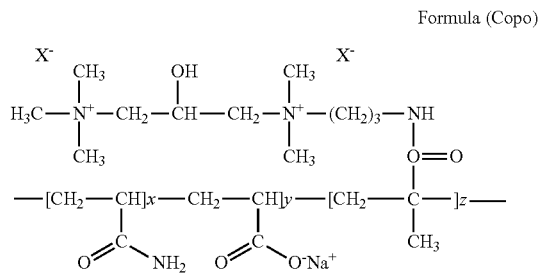

wherein:

$x+y+z=Q$

Q stands for values from about 3 to about 55000, preferably from about 10 to about 25000, particularly preferably from about 50 to about 15000, further preferably from about 100 to about 10000, even further preferably from about 500 to about 8000 and in particular from about 1000 to about 5000,
x stands for (from about 0 to about 0.5) Q, preferably (from about 0 to about 0.3) Q and in particular for the values 0, 1, 2, 3, 4, 5, wherein the value 0 is preferred,
y stands for (from about 0.1 to about 0.95) Q, preferably for (from about 0.5 to about 0.7) Q and in particular for values from about 1 to about 24000, preferably from about 5 to about 15000, particularly preferably from about 10 to about 10000 and in particular from about 100 to about 4800,
z stands for (from about 0.001 to about 0.5) Q, preferably for (from about 0.1 to about 0.5) Q and in particular for values from about 1 to about 12500, preferably from about 2 to about 8000, particularly preferably from about 3 to about 4000 and in particular from about 5 to about 2000.

Regardless of which of the preferred copolymers having the formula (Copo) are used, preferred are hair treatment agents as contemplated herein which are exemplified in that the ratio of (y:z) is from about 4:1 to about 1:2, preferably from about 4:1 to about 1:1.

Regardless of which copolymers are used in the agents, preferred are hair treatment agents in which the copolymer has a molar mass from about 10000 to about 20 million $gmol^{-1}$, preferably from about 100000 to about 10 million $gmol^{-1}$, further preferably from about 500000 to about 5 million $gmol^{-1}$ and in particular from about 1.1 million to about 2.2 million $gmol^{-1}$.

A most preferred copolymer which is constructed as depicted previously is available commercially under the designation Polyquaternium-74.

A particularly suitable homopolymer is the optionally cross-linked, poly(methacryloyl oxyethyltrimethyl ammonium chloride) having the INCI designation Polyquaternium-37. Such products are available commercially under the designations Cosmedia® CTH or Cosmedia® Ultragel 300 (BASF SE) or Synthalen® CR (3V Group).

The homopolymer is preferably used in the form of a nonaqueous polymer dispersion. Such polymer dispersions are available commercially under the designations Salcare® SC 95 and Salcare® SC 96. Also suitable is a polymer dispersion which is marketed under the designation Cosmedia® Triple C (ex BASF SE).

Suitable cationic polymers which are derived from natural polymers are cationic derivatives of polysaccharides, for example, cationic derivatives of cellulose, starch or guar. Also suitable are chitosan and chitosan derivatives.

Cationic polysaccharides have the general formula G-O—B—N+$R_aR_bR_c$$A^-$
G is an anhydroglucose group, for example, starch or cellulose anhydroglucose;
B is a divalent compound group, for example, alkylene, oxyalkylene, polyoxyalkylene or hydroxyalkylene;
$R_a$, $R_b$ and $R_c$ are independently of one another alkyl, aryl, alkylaryl, arylalkyl, alkoxyalkyl or alkoxyaryl each having up to about 18 C atoms, wherein the total number of C atoms in $R_a$, $R_b$ and $R_c$ is preferably a maximum of about 20;
$A^-$ is a usual counter anion and is preferably chloride.

Cationic, i.e. quaternized celluloses are available on the market with a different degree of substitution, cationic charge density, nitrogen content and molecular weights. For example, Polyquaternium-67 is supplied in the trade under the designations SoftCat® Polymer SL or SoftCat® Polymer SK (Dow). Another highly preferred cellulose is offered under the trade name Mirustyle® CP made by Croda. This is a Trimonium and Cocodimonium hydroxyethyl cellulose derivatized cellulose with the INCI designation polyquaternium-72. Polyquaternium-72 can be used both in solid form and also already pre-dissolved in aqueous solution.

Other cationic celluloses are Ucare® Polymer JR 400 (Dow, INCI designation Polyquaternium-10) as well as Polymer Quatrisoft® LM-200 (Dow, INCI designation Polyquaternium-24). Other commercial products are the compounds Celquat® H 100 and Celquat® L 200. Particularly preferred cationic celluloses are Polyquaternium-24, Polyquaternium-67 and Polyquaternium-72.

Suitable cationic guar derivatives are distributed under the tradename Jaguar® and have the INCI-designation Guar Hydroxypropyltrimonium Chloride. Furthermore particularly suitable cationic guar derivatives are available from Hercules under the designation N-Hance®. Further cationic guar derivatives are marketed by BASF SE under the designation Cosmedia®. A preferred cationic guar derivative is the commercial product AquaCat® from Hercules. This raw material is an already pre-dissolved cationic guar derivative. The cationic guar derivatives are preferred.

A suitable chitosan is distributed for example by Kyowa Oil& Fat, Japan, under the trade name Flonac®. A preferred chitosan salt is chitosonium pyrrolidone carboxylate, which is distributed for example under the designation Kytamer® PC by Amerchol, USA. Further chitosan derivatives are freely available commercially under the trade names Hydagen® CMF, Hydagen® HCMF and Chitolam® NB/101.

Another group of polymers which can be used exceptionally well are polymers based on glucose. The following diagram shows a cationic alkyloligoglucoside of this type.

and more preferred here are those technical fatty alcohol sections which are of plant origin. The counterion to the cationic charge is a physiologically compatible anion, for example, halide, methosulphate, phosphate, citrate, tartrate etc. Preferably the counterion is a halide such as fluoride, chloride, bromide or methosulphate. Most preferably the anion is chloride.

Particularly preferred examples for the cationic alkyloligoglucosides are compounds having the INCI-designations Polyquaternium-77, Polyquaternium-78, Polyquaternium-79, Polyquaternium-80, Polyquaternium-81 and Polyquaternium-82. Most preferred are the cationic alkyloligoglucosides having the designations Polyquaternium-77, Polyquaternium-81 and Polyquaternium-82.

Compounds of this type can be obtained for example under the designation Poly Suga® Quat from Colonial Chemical Inc.

Naturally it is also included that more mixtures of cationic alkyloligoglucosides can be used. It is preferred in this case if one long-chain and one short-chain cationic alkyloligoglucoside can be used simultaneously in this case.

A further preferred cationic polymer can be obtained on the basis of ethanolamine. The polymer is available commercially under the designation Polyquaternium-71.

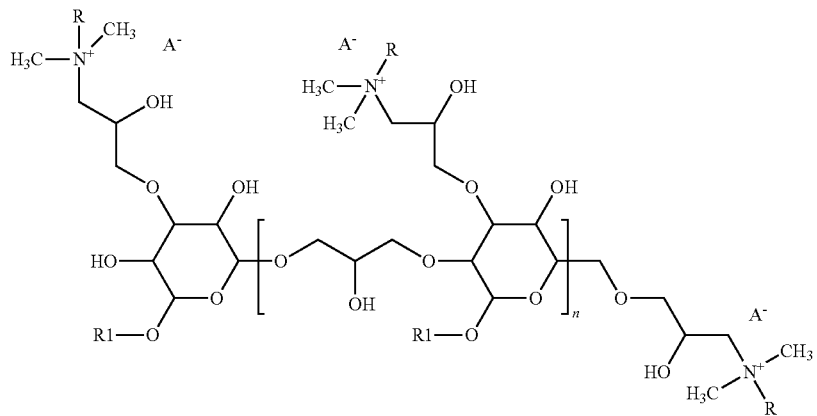

In the previously depicted formula the groups R stand independently of one another for a linear or branched C6 to C30 alkyl group, a linear or branched C6-C30 alkenyl group, preferably the group R stands for a group R selected from: lauryl, myristyl, cetyl, stearyl, oleyl, behenyl or arachidyl.

The groups R1 stand independently of one another for a linear or branched C6 to C30 alkyl group, a linear or branched C6-C30 alkenyl group, preferably the group R stands for a group R selected from: butyl, capryl, caprylyl, octyl, nonyl, decanyl, lauryl, myristyl, cetyl, stearyl, oleyl, behenyl or arachidyl. Particularly preferably the groups R1 are the same. Even more preferably the groups R1 are selected from technical mixtures of fatty alcohol sections of C6/C8-fatty alcohols, C8/C10-fatty alcohols, C10/C12-fatty alcohols, C12/C14-fatty alcohols, C12/C18-fatty alcohols,

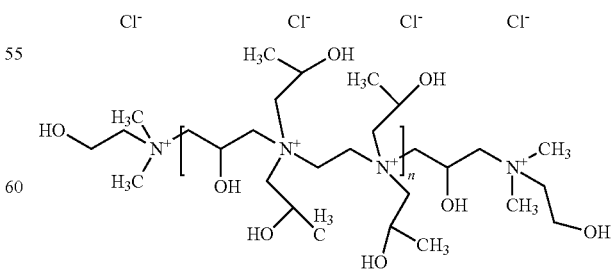

This polymer can be obtained, for example, under the designation Cola® Moist 300 P from Colonial Chemical Inc.

Furthermore, a cationic alkyloligoglucoside, as shown in the following diagram can be used.

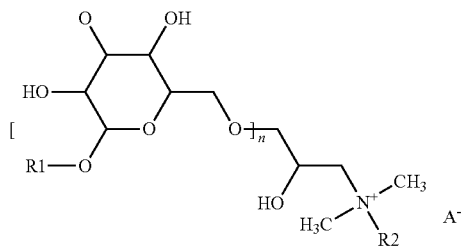

In the previously depicted formula the group R2 stands for a linear or branched C6 to C30 alkyl group, a linear or branched C6-C30 alkenyl group, preferably the group R stands for a group R selected from: lauryl, myristyl, cetyl, stearyl, oleyl, behenyl or arachidyl. The group R1 stands for a linear or branched C6 to C30 alkyl group, a linear or branched C6 to C30 alkenyl group, preferably the group R1 stands for a group R selected from: butyl, capryl, caprylyl, octyl, nonyl, decanyl, lauryl, myristyl, cetyl, stearyl, oleyl, behenyl or arachidyl. More preferably the group R1 is selected from technical mixtures of fatty alcohol sections of C6/C8-fatty alcohols, C8/C10-fatty alcohols, C10/C12-fatty alcohols, C12/C14-fatty alcohols, C12/C18-fatty alcohols, and more preferred here are those technical fatty alcohol sections which are of plant origin. The index n stands for a number between from about 1 and about 20, preferably between from about 1 and about 10, preferably between from about 1 and about 5, and most preferably between from about 1 and about 3. The counterion to the cationic charge A⁻ is a physiologically compatible anion, for example, halide, methosulphate, phosphate, citrate, tartrate etc. Preferably the counterion is a halide such as fluoride, chloride, bromide or methosulphate. Most preferably the anion is chloride.

Particularly preferred examples for the cationic alkyloligoglucosides are the compounds having the INCI designations laurdimoniumhydroxypropyl decylglucosides chloride, laurdimoniumhydroxypropyl laurylglucosides chloride, stearyldimoniumhydroxypropyl decylglucosides chloride, stearyldimoniumhydroxypropyl laurylglucosides chloride, stearyldimoniumhydroxypropyl laurylglucosides chloride or cocoglucosides hydroxypropyltrimonium chloride.

Such compounds can be obtained for example under the designation Suga® Quat from Colonial Chemical Inc.

Naturally it is also included that more mixtures of cationic alkyloligoglucosides can be used. It is preferred in this case if one long-chain and one short-chain cationic alkyloligoglucoside can be used simultaneously.

A further preferred cationic polymer comprises at least one structural unit having the formula (IV), at least one structural unit having the formula (V), at least one structural unit having the formula (VI) and at least one structural unit having the formula (VII).

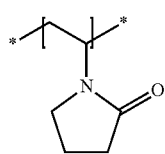 (IV)

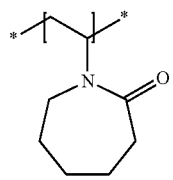 (V)

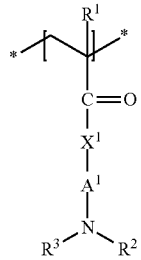 (VI)

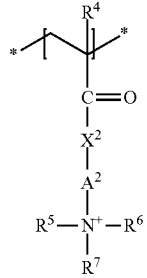 (VII)

wherein
$R^1$ and $R^4$ stand independently of one another for a hydrogen atom or a methyl group,
$X^1$ and $X^2$ stand independently of one another for an oxygen atom or an NH group,
$A^1$ and $A^2$ stand independently of one another for a group ethan-1,2-diyl, propan-1,3-diyl or butan-1,4-diyl,
$R^2$, $R^3$, $R^5$ and $R^6$ stand independently of one another for a ($C_1$ to $C_4$) alkyl group,
$R^7$ stands for a ($C_8$ to $C_{30}$) alkyl group.

According to the above formulae and all the following formulae, a chemical bond exemplified by the symbol *stands for a free valency of the corresponding structural fragment.

All possible physiologically compatible anions such as, for example chloride, bromide, hydrogen sulphate, methylsulphate, ethyl sulphate, tetrafluoroborate, phosphate, hydrogen phosphate, dihydrogen phosphate or p-toluolsulphonate, triflate are used to compensate for the positive polymer charge in the agent.

Examples for ($C_1$ to $C_4$) alkyl groups as contemplated herein are methyl, ethyl, propyl, isopropyl, butyl, sec-butyl, isobutyl, tert-butyl.

Example for ($C_8$ to $C_{30}$) alkyl groups are octyl (capryl), decyl (caprinyl), dodecyl (lauryl), tetradecyl (myristyl), hexadecyl (cetyl), octadecyl (stearyl), eicosyl (arachyl), docosyl (behenyl).

The following cationic polymers can be used in the agents when the cationic polymers satisfy one or more of the following features in relation to the aforesaid formulae (IV) to (VII):
$R^1$ and $R^4$ each mean a methyl group,
$X^1$ stands for an NH group,
$X^2$ stands for an NH group, A¹ and A² stand independently of one another for ethan-1,2-diyl or propan-1,3-diyl, $R^2$, $R^3$, $R^5$ and $R^6$ stand independently of one another for methyl or ethyl, (particularly preferably for methyl), $R^7$ stands for an ($C_{10}$ to $C_{24}$) alkyl group, in particular for decyl (caprinyl), dodecyl (lauryl), tetradecyl (myristyl), hexadecyl (cetyl), octadecyl (stearyl), eicosyl (arachyl) or docosyl (behenyl).

It is preferable to select the structural unit having the formula (VI) from at least one structural unit having the formulae (VI-1) to (VI-8)

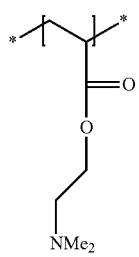
(VI-1)

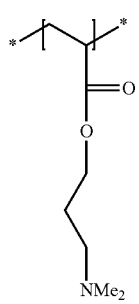
(VI-2)

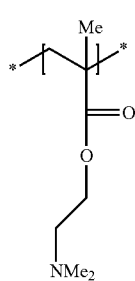
(VI-3)

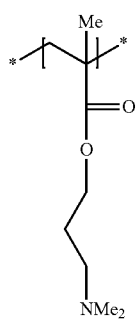
(VI-4)

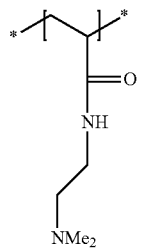
(VI-5)

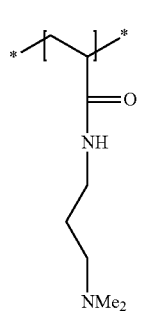
(VI-6)

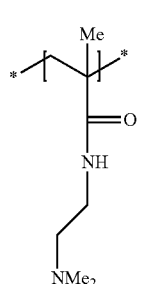
(VI-7)

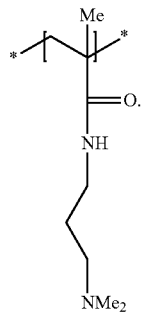
(VI-8)

In addition, it proves to be particularly preferred to select the structural unit according to formula (VI-7) and/or formula (VI-8) as the structural unit according to formula (VI). The structural unit of formula (VI-8) is a quite particularly preferred structural unit.

Furthermore, with a view to solving the object it was found to be preferably if the structural unit of formula (VII) is selected from at least one structural unit of formulae (VII-1) to (VII-8)

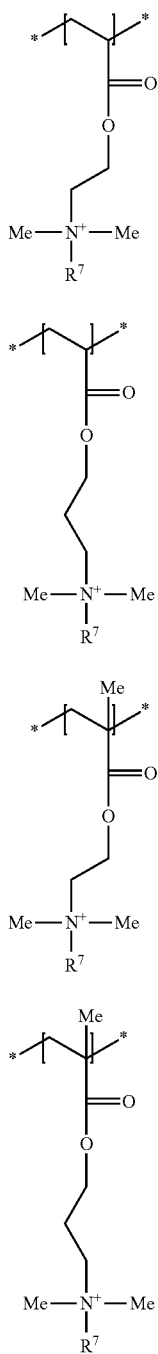
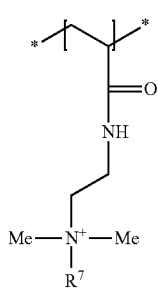
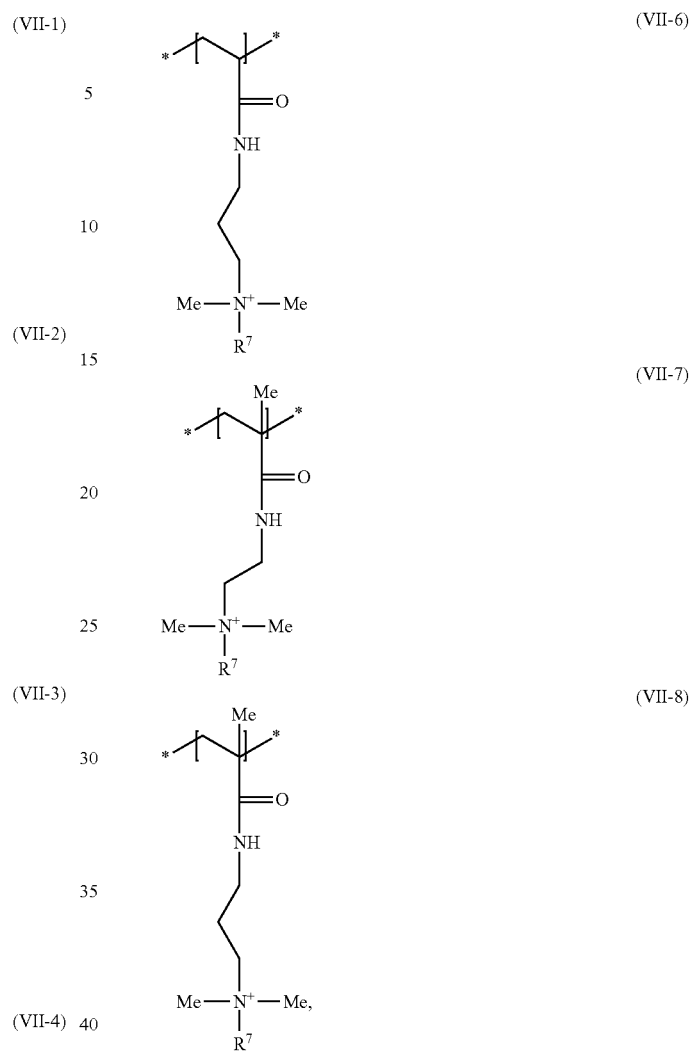

wherein $R^7$ in each case stands for a ($C_8$ to $C_{30}$) alkyl group.

The structural units of formula (VII-7) and/or formula (VII-8) are again held to be a particularly preferred structural unit of formula (VII), wherein in each case $R^7$ stands for octyl (capryl), decyl (caprinyl), dodecyl (lauryl), tetradecyl (myristyl), hexadecyl (cetyl), octadecyl (stearyl), eicosyl (arachyl) or docosyl (behenyl). The structural unit of formula (VII-8) is a quite particularly preferred structural unit of formula (VII).

A quite particularly preferred cationic polymer contained in the agent comprises at least one structural unit of formula (IV), at least one structural unit of formula (V), at least one structural unit of formula (VI-8) and at least one structural unit of formula (VII-8),

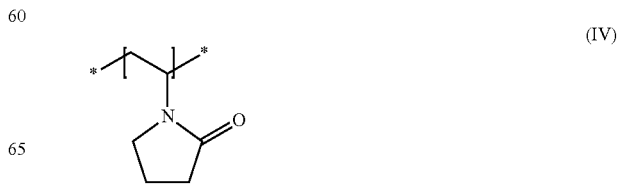

-continued

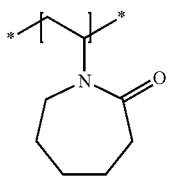
(V)

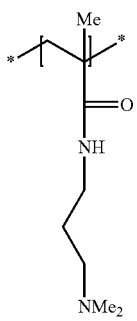
(VI-8)

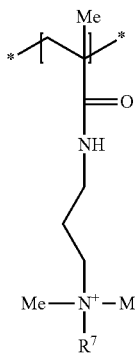
(VII-8)

wherein R⁷ stands for octyl (capryl), decyl (caprinyl), dodecyl (lauryl), tetradecyl (myristyl), hexadecyl (cetyl), octadecyl (stearyl), eicosyl (arachyl) or docosyl (behenyl).

A quite particularly preferred cationic polymer is the copolymer of N-vinylpyrrolidone, N-vinylcaprolactam, N-(3-dimethylaminopropyl)methacrylamide and 3-(methacryloylamino)propyl-lauryl-dimethylammoniumchloride (INCI designation: Polyquaternium-69), which for example is marketed under the trade name AquaStyle® 300 (28-32 wt. % active substance in ethanol-water mixture, molecular weight 350,000) by ISP.

Further preferred cationic polymers are for example cationized honey, for example the commercial product Honeyquat® 50, polymeric dimethyldiallyl ammonium salts and copolymers thereof with esters and amides of acrylic acid and methacrylic acid. The products available commercially under the designations Merquat® 100 (poly(dimethyldiallyl ammonium chloride)) and Merquat® 550 (dimethyldiallyl ammonium chloride acrylamide copolymer) are example for such cationic polymers with the INCI designation Polyquaternium-7, Vinylpyrrolidone vinylimidazolium methochloride copolymers, as supplied under the designations Luviquat® FC 370, FC 550 and the INCI designation Polyquaternium-16 as well as FC 905 and HM 552, quaternized vinylpyrrolidone/dimethyl aminoethyl methacrylate for example vinylpyrrolidone/dimethyl aminoethyl methacrylate methosulphate copolymer, which is distributed under the trade names Gafquat® 755 N and Gafquat® 734 by Gaf Co., USA and the INCI-designation Polyquaternium-11, quaternized polyvinylalcohol, as well as the polymers known under the designations Polyquaternium-2, Polyquaternium-17, Polyquaternium-18 and Polyquaternium-27 with quaternary nitrogen atoms in the polymer main chain, Vinylpyrrolidone vinylcaprolactam acrylate terpolymers, as supplied commercially with acrylic acid groups and acrylic amide groups as third monomer block for under the designation Aquaflex® SF 40.

If the hair treatment agent is assembled as a care rinse, it preferably contains at least one cationic tenside or a cationic polymer in a preferred weight fraction of preferably from about 0.01 to about 5 wt. %, more preferably from about 0.05 to about 2 wt. %, and particularly preferably from about 0.1 to about 0.5 wt. %, wherein the quantitative details relate to the total weight of the hair treatment agent.

It has been shown that the use of the aforesaid salt-containing components in the hair treatment agents imparts exceptional properties. Thus, the colour change of the artificially produced hair colour is extremely small after several treatment processes. In addition, the hair treatment agents increase the elasticity of the hair treated therewith and result in an internal structural strengthening of the hair fibres which is reflected for example in higher melting temperatures (=denaturing temperatures) in a differential thermal analysis.

It has been found that it is particularly effective and the colour change of the artificially produced hair colour is particularly small after several washing processes of the hair treatment agents contain a mixture of stearic acid and lanthanum chloride, a mixture of stearic acid and strontium lactate or strontium stearate.

The hair treatment agents can in principle be applied to hair that has been coloured with permanent, semi-permanent or temporary hair colours. However, temporary hair colours are intended to be washed out with time and/or to fade which is why the hair treatment agent is particularly suitable for application to hair that has been coloured with permanent or oxidative hair colourants.

In addition to the aforesaid ingredients, the hair treatment agents can contain further ingredients which are usual in the respective applications.

The effectiveness of the hair treatment agents can be increased still further if a special hair-conditioning active substance is added to it. In particular, the colour brilliance of the artificially produced hair colour can thereby be stabilized and maintained. The hair treatment agents therefore additionally contain at least one hair-conditioning active substance in a weight fraction of from about 0.01 to about 10 wt. % of the total weight of the hair treatment agent. Suitable hair-conditioning active substances are preferably understood as natural, mineral or synthetic oil, fat or wax components, vitamins and/or protein hydrolysates. Within the framework of the present disclosure, cationic polymers do not belong to the hair-conditioning active substances. By using a plant oil and/or a silicone as hair-conditioning active substance, not only the colour brilliance of the hair can be particularly well stabilized but in addition the haptic properties such as the hold and the sleekness of the coloured hair can be improved.

Further suitable ingredients comprise non-ionic tensides, amphoteric/zwitterion tensides, non-ionic polymers, anionic polymers, amino acids, oligopeptides, provitamins, vitamin precursors, betaine, bioquinone, purine(derivatives), taurine (derivatives), L-carnitine(salts), panthenol, panthothenic acid, 2-furanone, 2-furanone derivative, ectoine, allantoine, plant extracts, ester oils, UV-light protection filters, structuring agents, thickeners, electrolyte, pH-regulating agents, expanding agents, dyes, anti-dandruff agents, complex forming agents, opacifiers, pearl shine agents, pigments, stabilizing agents, propellants, antioxidants, perfumed oils, and/or preserving agents.

A further subject matter of the present disclosure is a method for reducing and/or avoiding bleeding out and/or fading of artificially produced hair colours and/or for strengthening the internal hair structure. comprising the following steps:

applying a hair treatment agent to the—preferably wet—dyed-blond and/or coloured hair, allowing the agent to act for a period of at least about 5 seconds, optionally: rinsing out the composition with water, the hair treatment agent—relative to its weight—contains:
a) from about 1 to about 15 wt. % of a salt-containing component comprising
 (i) at least one polyvalent salt of a fatty acid and/or
 (ii) at least one fatty acid (A1) and at least one polyvalent salt (A2),
b) at least one cationic compound selected from
cationic tensides of the group formed from quaternary ammonium compounds, esterquats and/or amidoamines and/or
cationic polymers.

In a first preferred embodiment the method comprises the following steps
i. applying a hair rinse or a hair conditioner as hair treatment agent to the wet blond-dyed and/or coloured hair,
ii. allowing the hair rinse or hair conditioner to act for a period of from about 5 seconds to about 5 minutes,
iii. rinsing out the hair rinse or the hair conditioner with water.

In a second preferred embodiment the method comprise the step of applying a hair (care) spray or hair wax as hair treatment agent to the dry, blond-dyed or coloured hair.

A further subject matter of the present disclosure is the use of the hair treatment agent for reducing and/or avoiding the bleeding out and/or fading of artificially produced hair colours and/or for improving the colour intensity and/or the colour fidelity and for improving at least one of the properties, tensile strength of keratin fibres, in particular of human hair;
combability of keratin fibres, in particular of human hair;
hydrophobizing the surface of keratin fibres, in particular of human hair;
strengthening the internal structure of keratin fibres, in particular of human hair.

EXAMPLES

1) Exemplary Embodiments the following hair treatment agents were produced (the quantitative information relates to wt. %):

TABLE 1

| | Conditioner | | |
|---|---|---|---|
| | Conditioner 1 | Conditioner 2 | Conditioner 3 |
| Cetearyl alcohol | 2.50 | 1.50 | 2.00 |
| Quaternium-87 | 4.00 | 4.00 | 4.00 |
| Lactic acid | 1.00 | 0.7 | 2.36 |

TABLE 1-continued

| | Conditioner | | |
|---|---|---|---|
| | Conditioner 1 | Conditioner 2 | Conditioner 3 |
| Isopropyl myristate | 0.80 | 1.00 | 0.80 |
| Distearoylethyl Hydroxyethylmonium methosulphate | 1.00 | 1.00 | 1.00 |
| Stearic acid | 3.00 | — | 3.00 |
| Lanthanum chloride heptahydrate | 0.75 | — | — |
| Strontium hydroxide | — | — | 0.90 |
| Strontium stearate | — | 4.00 | — |
| Phenoxyethanol | 0.40 | 0.40 | 0.40 |
| Stearamidopropyl dimethylamine | 0.40 | 0.40 | 0.40 |
| Sodium methylparaben | 0.30 | 0.30 | 0.30 |
| Polyquaternium-37 | 0.50 | 0.50 | 0.50 |
| Panthenol | 0.20 | 0.20 | 0.20 |
| Apricot kernel oil | 0.20 | — | 0.20 |
| Hydrolyzed keratin | 0.30 | 0.30 | 0.30 |
| NaOH | 0.40 | — | — |
| Perfume | 0.45 | 0.45 | 0.45 |
| Water | ad 100 | ad 100 | Ad 100 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair treatment agent for reducing and/or avoiding bleeding out and/or fading of artificially produced hair colours and/or for strengthening the internal hair structure, comprising—relative to the total quantity of hair treatment agent—
 a) from about 1 to about 15 wt. % of a salt-containing component consisting of:
  (i) one polyvalent salt of a fatty acid consisting of a lanthanum or a strontium salt of a fatty acid or
  (ii) at least one fatty acid (A1) and one polyvalent salt (A2) consisting of a lanthanum or a strontium salt,
 b) at least one cationic compound comprising a quaternary ammonium compound, an esterquat and an amidoamine,
 wherein the one polyvalent salt of the fatty acid or the one polyvalent salt (A2) consist of an entirety of the polyvalent salt of fatty acid compounds or polyvalent salt compounds present in the hair treatment agent.

2. The hair treatment agent according to claim 1, wherein the hair treatment agent comprises as salt-containing component a)(i) a polyvalent salt of a fatty acid selected from the group of dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, palmitoleic acid, petroselinic acid, elaidinic acid, oleic acid, erucic acid, linoleic acid, and linolenic acid.

3. The hair treatment agent according to claim 1, wherein the fatty acid (A1) of the salt-containing component a)(ii) is selected from the group of dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, palmitoleic acid, petroselinic acid, elaidinic acid, oleic acid, erucic acid, linoleic acid, and linolenic acid.

4. The hair treatment agent according to claim 1, wherein the polyvalent salt (A2) of the salt-containing component a)(ii) is an anion selected from the group of halides, hydroxides, sulphates, nitrates, triflates, borates, citrates, tartrates, lactates, malates, salicylates, aspartates, arginates, fumarates, and maleates.

5. The hair treatment agent according to claim 1, wherein the polyvalent salt (A2) of the salt-containing component a)(ii) consists of a strontium or lanthanum halide.

6. The hair treatment agent according to claim 1, wherein the hair treatment agent consists of
as salt-containing component a)(i) strontium stearate or
as salt-containing component a)(ii)(A1) octadecanoic acid and as salt-containing component a)(ii)(A2) lanthanum chloride or strontium lactate.

7. The hair treatment agent according to claim 1, wherein the polyvalent salt (A2) of the salt-containing component a)(ii) consists of a strontium or lanthanum chloride or a strontium or lanthanum lactate.

8. The hair treatment agent according to claim 1, wherein the salt-containing component a)(i)—consists of strontium stearate.

9. The hair treatment agent according to claim 1, wherein the salt-containing component a)(i) consists of strontium stearate, the salt-containing component a)(ii)(A1) consists of octadecanoic acid, and the salt-containing component a)(ii)(A2) consists of lanthanum chloride or strontium lactate.

10. The hair treatment agent according to claim 1, wherein the salt-containing component a)(i) consists of strontium stearate, the salt-containing component a)(ii)(A1) consists of octadecanoic acid, and the salt-containing component a)(ii)(A2) consists of lanthanum chloride.

11. The hair treatment agent according to claim 1, wherein the salt-containing component a)(i) consists of strontium stearate, the salt-containing component a)(ii)(A1) consists of octadecanoic acid, and the salt-containing component a)(ii)(A2) consists of strontium lactate.

12. The hair treatment agent according to claim 1, wherein the salt-containing component a)(ii)(A1) consists of octadecanoic acid and the salt-containing component a)(ii)(A2) consists of lanthanum chloride or strontium lactate.

13. The hair treatment agent according to claim 1, comprising
relative to its weight:
from about 2 to about 8 wt. % of the salt-containing component a)(i); or
from about 2 to about 4 wt. % of fatty acid (A1) as constituent of the salt-containing component a)(ii); and
from about 0.5 to about 3 wt. % of polyvalent salt (A2) as constituent of the salt-containing component a)(ii).

14. The hair treatment agent according to claim 1, wherein the quaternary ammonium compound comprises an imidazolinium compound, the esterquat comprises a methyl-N,N-bis(stearoyloxyethyl)-N-(2-hydroxyethyl)ammonium compound, and the amidoamine comprises an alkyl amidoamine produced by amidization of a natural or synthetic fatty acid or fatty acid section with a dialkyl aminoamine.

15. The hair treatment agent according to claim 14, wherein the quaternary ammonium compound, the esterquat, and the amidoamine are each present in an amount of about 0.01 to about 5 wt.-%, based on the total weight of the agent.

16. The hair treatment agent according to claim 15, further comprising a poly(methacryloyl oxyethyltrimethyl ammonium chloride) in an amount of about 0.01 to about 5 wt.-%, based on the total weight of the agent.

17. A method for reducing and/or avoiding bleeding out and/or fading of dyed-blond and/or artificially produced hair colours and/or for strengthening the internal hair structure, comprising the following steps:
applying a hair treatment agent to the dyed-blond and/or coloured hair,
allowing the agent to act for a period of at least about 5 seconds,
optionally: rinsing the agent out of the hair with water, wherein
the hair treatment agent—relative to its weight—comprises:
a) from about 1 to about 15 wt. % of a salt-containing component consisting of:
(i) one polyvalent salt of a fatty acid consisting of a lanthanum or a strontium salt of a fatty acid or
(ii) at least one fatty acid (A1) and at least one polyvalent salt (A2) consisting of a lanthanum or a strontium salt,
b) at least one cationic compound comprising a quaternary ammonium compound, an esterquat and an amidoamine,
wherein the one polyvalent salt of the fatty acid or the one polyvalent salt (A2) consist of an entirety of the polyvalent salt of fatty acid compounds or polyvalent salt compounds present in the hair treatment agent.

* * * * *